(12) United States Patent
Engel et al.

(10) Patent No.: US 7,605,121 B2
(45) Date of Patent: Oct. 20, 2009

(54) OLIGOPEPTIDE LYOPHILISATE, THEIR PREPARATION AND USE

(75) Inventors: Jürgen Engel, Alzenau (DE); Burkhard Wichert, Bielefeld (DE); Dieter Sauerbier, Halle (DE); Gudrun Sauerbier, legal representative, Halle (DE); Thomas Reissmann, Lüneberg (DE)

(73) Assignee: AEterna Zentaris GmbH, Frankfurt (DE)

( * ) Notice: Subject to any disclaimer, the term of this patent is extended or adjusted under 35 U.S.C. 154(b) by 0 days.

(21) Appl. No.: 11/039,997

(22) Filed: Jan. 24, 2005

(65) Prior Publication Data

US 2005/0124546 A1 Jun. 9, 2005

Related U.S. Application Data

(60) Continuation of application No. 10/153,640, filed on May 24, 2002, now Pat. No. 6,867,191, which is a division of application No. 10/040,457, filed on Jan. 9, 2002, now Pat. No. 6,863,891, which is a division of application No. 08/468,145, filed on Jun. 6, 1995, now Pat. No. 6,828,415, which is a continuation-in-part of application No. 08/198,037, filed on Feb. 22, 1994, now abandoned.

(30) Foreign Application Priority Data

Feb. 19, 1993 (DE) .................................. P4305225

(51) Int. Cl.
A61K 39/38 (2006.01)
A61K 39/385 (2006.01)
A61K 39/00 (2006.01)
A61K 38/00 (2006.01)
A61K 38/24 (2006.01)
A01N 37/18 (2006.01)

(52) U.S. Cl. ............................ 514/2; 514/15; 514/800; 424/184.1; 424/193.1; 424/198.1; 930/20; 930/110; 930/130; 530/300; 530/313

(58) Field of Classification Search ....................... None
See application file for complete search history.

(56) References Cited

U.S. PATENT DOCUMENTS

| | | | |
|---|---|---|---|
| 3,816,386 A | 6/1974 | Hedlund et al. | |
| 4,372,884 A | 2/1983 | Brown et al. | |
| 4,504,414 A * | 3/1985 | Folkers et al. | 530/313 |
| 4,512,923 A | 4/1985 | Flegel et al. | |
| 4,565,804 A | 1/1986 | Rivier et al. | |
| 4,693,993 A | 9/1987 | Stewart et al. | |
| 4,701,499 A | 10/1987 | Kornreich et al. | |
| 4,711,877 A | 12/1987 | Moore | |
| 4,716,242 A | 12/1987 | Engel et al. | |
| 4,800,191 A | 1/1989 | Schally et al. | |
| 4,908,475 A | 3/1990 | Callahan et al. | |
| 5,198,533 A | 3/1993 | Schally et al. | |
| 5,204,335 A | 4/1993 | Sauerbier et al. | |
| 5,268,360 A | 12/1993 | Yashikawa et al. | |
| 5,446,033 A | 8/1995 | Engel et al. | |
| 5,663,145 A | 9/1997 | Engel et al. | |
| 5,728,738 A | 3/1998 | Engel et al. | |
| 5,750,131 A | 5/1998 | Wichert et al. | |
| 5,773,032 A | 6/1998 | Engel et al. | |
| 5,945,128 A | 8/1999 | Deghenghi | |
| 5,968,895 A | 10/1999 | Gefter et al. | |
| 5,998,377 A | 12/1999 | Engel et al. | |
| 6,022,860 A | 2/2000 | Engel et al. | |
| 6,054,555 A | 4/2000 | Engel et al. | |
| 6,106,805 A | 8/2000 | Engel et al. | |
| 6,300,313 B1 * | 10/2001 | Engel et al. | 514/15 |
| 6,319,192 B1 * | 11/2001 | Engel et al. | 600/33 |
| 6,627,609 B1 * | 9/2003 | Bernd et al. | 514/15 |
| 6,740,634 B1 * | 5/2004 | Saikawa et al. | 514/2 |
| 6,780,972 B2 * | 8/2004 | Damm et al. | 530/345 |
| 6,828,415 B2 * | 12/2004 | Engel et al. | 530/300 |
| 6,867,191 B2 * | 3/2005 | Engel et al. | 514/15 |
| 7,005,418 B1 * | 2/2006 | Riethmuller-Winzen et al. | 514/12 |
| 7,098,305 B2 * | 8/2006 | Deghenghi et al. | 530/326 |
| 7,148,195 B2 * | 12/2006 | Bernd et al. | 514/15 |
| 7,214,662 B2 * | 5/2007 | Sarlikiotis et al. | 514/14 |
| 7,300,935 B2 * | 11/2007 | Cho et al. | 514/252.02 |
| 7,388,032 B2 * | 6/2008 | Saikawa et al. | 514/772.1 |
| 7,393,834 B2 * | 7/2008 | Bouchard et al. | 514/16 |
| 2002/0099018 A1 * | 7/2002 | Engel et al. | 514/14 |
| 2002/0103113 A1 * | 8/2002 | Engel et al. | 514/2 |
| 2002/0198146 A1 * | 12/2002 | Damm et al. | 514/12 |
| 2002/0198186 A1 * | 12/2002 | Engel et al. | 514/200 |

(Continued)

FOREIGN PATENT DOCUMENTS

| | | |
|---|---|---|
| DE | 141 996 | 6/1980 |
| EP | 88-308573 | 9/1988 |
| WO | WO 91/19743 A2 * | 12/1991 |
| WO | WO 94/13313 A1 * | 6/1994 |
| WO | WO 95/15767 A1 * | 6/1995 |

OTHER PUBLICATIONS

Szende et al, PNAS, USA, Feb. 1990, 87:901-903.*
Weinbauer et al, Recent Results in Cancer Research, 1992, 124:113-136.*
Bajusz et al, Int. J. Peptide Protein Res., 1988, 32:425-435.*
Gonzalez-Barcena et al, the Prostate, 1994, 24:84-92.*
Schmidt et al, Contraception, Mar. 1984, 29/3:283-289.*
Hahn et al, Life Sciences, 1985, 37/6:505-514.*
Bajusz et al, PNAS, USA, Mar. 1998, 85:1637-1641.*
Lizio et al, Pharmaceutical Research, 2001, 18/6:771-779.*
Seelig et al, Fertility and Sterility, Mar. 2002, 77/3:472-475.*
Reissmann et al, European J. Cancer, 1996, 32A/9:1574-1579.*
Lizio et al, European J. Pharmaceutical Sciences, 2001, 9:253-258.*

(Continued)

Primary Examiner—N. M Minnifield
(74) Attorney, Agent, or Firm—Pillsbury Winthrop Shaw Pittman LLP

(57) ABSTRACT

A novel lyophilizate and method of preparation as well as the use of the lyophilizate to treat female infertility and for gonad protection. Cetrorelix is dissolved in acetic acid 30% v/v, the solution is transferred to water and freeze dried.

4 Claims, No Drawings

U.S. PATENT DOCUMENTS

| | | | |
|---|---|---|---|
| 2003/0100509 | A1* | 5/2003 | Sarlikiotis et al. ............. 514/15 |
| 2004/0138138 | A1* | 7/2004 | Engel et al. .................... 514/16 |
| 2004/0259801 | A1* | 12/2004 | Damm et al. ................. 514/15 |
| 2004/0266695 | A1* | 12/2004 | Bernd et al. ................... 514/15 |
| 2005/0032831 | A1* | 2/2005 | Kozikowski et al. ........ 514/311 |
| 2005/0049200 | A1* | 3/2005 | Bouchard et al. ............. 514/16 |
| 2005/0124546 | A1* | 6/2005 | Engel et al. ................... 514/14 |
| 2005/0159335 | A1* | 7/2005 | Bauer et al. ..................... 514/2 |
| 2006/0281685 | A1* | 12/2006 | Bernd et al. ................... 514/15 |
| 2007/0161571 | A1* | 7/2007 | Sarlikiotis et al. ............. 514/15 |
| 2007/0196416 | A1* | 8/2007 | Li et al. ....................... 424/422 |
| 2008/0145383 | A1* | 6/2008 | Zauner et al. ............ 424/208.1 |
| 2008/0255053 | A1* | 10/2008 | Riethmuller-Winzen et al. ............................ 514/15 |

OTHER PUBLICATIONS

Riethmuller-Winzen et al, International J. Gynecology & Obsterics, 2000, 70/Suppl. 1:A97, Abstract # P1.06.19.*

Ludwig et al Eur. J. Obst. & Gyn. and Reprod. Biology, 2000, 89:177-179.*

Grundker et al, Gynecologic Oncology, 2000, 78:194-202.*

Soderhall et al, BBRC, 2005, 333:568-582.*

Grohganz et al, Eur. J. Pharmaceutics and Biopharmaceutics, 2005, 59:439-448.*

Verschragen et al, Gynecologic Oncology, 2003, 90:552-559.*

Erb et al, Fertility and Sterility, Feb. 2001, 75/2:316-323.*

Zijlstra et al, Eur. J. Pharmaceutical Sciences, 2004, 23:139-149.*

Olivennes et al, Human Reproduction, 1995, 10/6:1382-1386.*

Srkalovic et al, Endocrinology, 1990, 127/6:3052-3060.*

Behre et al, Clinical Endocriniolgy, 1994, 40:241-248.*

Leroy et al, Fertility and Sterility, Sep. 1994, 62/3:461-467.*

Norman, Current Opinion in Oncologic, Endocrine & Metabolic Investigational Drugs, 2000, 2/2:227-248.*

Albano et al., "The Luteal Phase of Nonsupplemented Cycles After Ovarian Superovulation With Human Menopausal Gonadotropin and the Gonadotropin-Releasing Hormone Antagonist Cetrorelix," *Fertility and Sterility*, vol. 70, No. 2, Aug. 1998, pp. 357-359.

Albano et al., "Ovarian Stimulation With HMG: Results of a Prospective Randomized Phase III European Study Comparing the Luteinizing Hormone-Releasing Hormone (LHRH)-Antagonist Cetrorelix and the LHRH-Agonist Buserelin," *Human Reproduction*, vol. 15, No. 3, 2000, pp. 526-531.

Albano et al., "Hormonal Profile During the Follicular Phase in Cycles Stimulated with a Combination of Human Menopausal Gonadotrophin and Gonadotrophin-Releasing Hormone Antagonist (Cetrorelix)," *Human Reproduction*, vol. 11, No. 10, 1996, pp. 2114-2118.

Craft et al., "Will GnRH Antagonists Provide New Hope For Patients Considered 'Difficult Responders' to GnRH Agonist Protocols?," *Human Reproduction*, vol. 14, No. 12, 1999, pp. 2959-2962.

Christin-Maltre et al., "Effect of Gonadotrophin-Releasing Hormone (GnRH) Antagonist During the LH Surge in Normal Women and During Controlled Ovarian Hyperstimulation," Clinical Endocrinology. vol. 52, 2000, pp. 721-726.

Diedrich et al., Suppression of the Endogenous Luteinizing Hormone Surge by the Gonadotrophin-Releasing Hormone Antagonist Cetrorelix During Ovarian Stimulation, *Human Reproduction*, vol. 9, No. 5, 1994, pp. 788-791.

Diedrich et al., "The Role of Gonadotropin-Releasing Hormone Antagonists in In Vitro Fertilization," *Seminars in Reproductive Medicine*, vol. 19, No. 3, 2001, pp. 213-220.

Felberbaum et al., "Ovarian Stimulation for In-Virtro Fertilization/Intracytoplasmic Sperm Injection With Gonadotrophins and Gonadotrophin-Releasing Hormone Analogues: Agonists and Antagonists," Human Reproduction, vol. 14, Suppl. 1, 1999, pp. 207-221.

Felberbaum et al., "Preserved Pituitary Response Under Ovarian Stimulation with HMG and GnRH Antagonists (Cetrorelix) in Women with Tubal Infertility," *European Journal of Obstetrics & Gynecology and Reproductive Biology*, vol. 61, 1995. pp. 151-155.

Felberbaum et al., "Ovarian Stimulation for Assisted Reproduction with HMG and Concomitant Midcycle Administration of the GnRH Antagonist Cetrorelix According to the Multiple Dose Protocol: A Prospective Uncontrolled Phase III Study." *Human Reproduction*, vol. 15, No. 5, 2000. pp. 1015-1020.

Fraser at al., "Control of the Preovulatory Luteinizing Hormone Surge by Gonadotropin-Releasing Hormone Antagonists," *Trends Endocrinol Metal*, vol. 5, No. 2, 1994, pp. 87-93.

Klingmoller et al., "Hormonal Responses to the New Potent GnRH Antagonist Cetrorelix," *Acta Endocrinologica*, No. 128, 1993, pp. 15-18.

Lin et al., "Is There a Difference in the Function of Granulosa-Luteal Cells in Patients Undergoing In-Vitro Fertilization Either With Gonadotrophin-Releasing Hormone Agonist or Gonadotrophin-Releasing Hormone Antagonist?," *Human Reproduction*, vol. 14, No. 4, 1999, pp. 885-888.

Ludwig et al., "Health of 227 Children Born After Controlled Ovarian Stimulation for In Vitro Fertilization Using the Luteinizing Hormone-Releasing Hormone Antagonist Cetrorelix," *Fertility and Sterility*, vol. 75, No. 1, 2001, pp. 18-22.

Ludwig et al., "Significant Reduction of the Incidence of Ovarian Hyperstimulation Syndrome (OHSS) by Using the LHRH Antagonist Cetrorelix (Cetrotide) in Contolled Ovarian Stimulation for Assisted Reproduction," *Arch Gynecol Obstet*, No. 264, 2000, pp. 29-32.

Mettler et al., "Cetrotide Confirmatory Trial of Cetrorelix/0.25 mg in 26 Women Undergoing Ovarian Stimulation with Recombinant Follicle Stimulating Hormones for IVF, ICSI and Embroy Transfer (ET)," *Clin. Exp. Obst. & Gyn.*, vol. XXVII, No. 2, 2000, pp. 103-105.

Nikolettos et al., "Gonadotropin-Releasing Hormone Antagonist Protocol: A Novel Method of Ovarian Stimulation in Poor Responders," European Journal of Obstetrics & Gynecology and Reproductive Biology, vol. 97, 2001, pp. 202-207.

Niwa et al., "Measurement of the Novel Decapeptide Cetrorelix in Human Plasma and Urine by Liquid Chromatography-Electrospray Ionization Mass Spectrometry," *Journal of Chromatography*, vol. B, No. 729, 1999, pp. 245-253.

Olivennes et al., "The Single or Dual Administration of the Gonadotropin-Releasing Hormone Antagonist Cetrorelix in an In Vitro Fertilization-Embryo Transfer Program," *Fertility and Sterility*, vol. 62, No. 3, 1994, pp. 468-476.

Olivennes et al., "GnRH Antagonist in Single-Dose Applications," *Human Reproduction Update*, vol. 6, No. 4, 2000, pp. 313-317.

Olivennes et al., "GnRH Antagonist in Single-Dose Applications," Infertility and Reproductive Medicine Clinics of North America, vol. 12, No. 1, 2001, pp. 119-128.

Oliveness et al., "Prospective, Randomized, Controlled Study of in Vitro Fertilization-Embryo Transfer With a Single Dose of a Luteinizing Hormone-Releasing Hormone (LH-RH) Antagonist (Cetrorelix) or a Depot Formula of an LH-RH Agonist (Triptorelin)," *Fertility and Sterility*, vol. 73, No. 2, 2000, pp. 314-320.

Ortmann at at., "Embryo Implantation and GnRH Antagonists," *Human Reproduction*, vol. 16, No. 4, 2001, pp. 608-611.

Rabasseda et al., "Ganirelix Acetate," *Drugs of the Future*, vol. 24, No. 4, 1999, pp. 393-403.

Reissmann et al., "Treatment of Experimental DMBA Induced Mammary Carcinoma with Cetrorelix (SB-75): A Potent Antagonist of Luteinizing Hormone-Releasing Hormone," *Cancer Research Clinical Oncology*, No. 118, 1992, pp. 44-49.

Reissmann et al., "Introduction of LHRH—Antagonists Into the Treatment of Gynaecological Disorders," *Human Reproduction*, vol. 9, No. 5, 1994, pp. 767-769.

Reissmann et al., "Development and Applications of Luteinizing Hormone-Releasing Hormone Antagonists in the Treatment of Infertility: An Overview," *Human Reproduction*, vol. 10, No. 8, 1995, pp. 1974-1981.

Rongieres-Bertrand et al., "Revival of the Natural Cycles in In-Vitro Fertilization with the Use of a New Gonadotrophin-Releasing Hormone Antagonist (Cetrorelix): A Pilot Study with Minimal Stimulation," *Human Reproduction*, vol. 14, No. 3, 1999, pp. 683-688.

Tavaniotou et al., "Comparison of LH Concentrations in the Early and Mid-Luteal Phase in IVF Cycles After Treatment with HMG Alone or in Association with the GnRH Antagonist Cetrorelix," *Human Reproduction*, vol. 16, No. 4, 2001, pp. 663-667.

Wikland et al., "A Prospective, Randomized Comparison of Two Starting Does of Recombinant FSH in Combination with Cetrorelix in Women Undergoing Ovarian Stimulation for IVF/ICSI," *Human Reproduction*, vol. 18, No. 8, 2001, pp. 1676-1681.

\* cited by examiner

OLIGOPEPTIDE LYOPHILISATE, THEIR PREPARATION AND USE

CROSS REFERENCES TO RELATED APPLICATIONS

This is a continuation of U.S. patent application Ser. No. 10/153,640, filed May 24, 2002, now U.S. Pat. No. 6,867,191 B2, which is a divisional of U.S. patent application Ser. No. 10/040,457 filed Jan. 9, 2002, now U.S. Pat. No. 6,863,891 B2, which is a divisional of U.S. patent application Ser. No. 08/468,145, filed on Jun. 6, 1995, now U.S. Pat. No. 6,828,415 B2, which is a continuation-in-part of U.S. patent application Ser. No. 08/198,037, filed Feb. 22, 1994, abandoned, which claims priority to German Patent Appl. No. P 4305225.8, filed Feb. 19, 1993.

The present invention relates to the preparation of a lyophilizate of a peptide and the use of the lyophilizate in the treatment of infertility and to provide male gonad protection.

BACKGROUND OF THE INVENTION

Cetrorelix is a decapeptide with a terminal acid amide group that is used in the form of its acetate salt. The synthesis and some pharmacological effects are described in European patent application 299 402 (U.S. Pat. No. 4,800,191).

It should be possible to administer the active substance subcutaneously in a dose of 0.1 to 20 mg. Aqueous solutions of the decapeptide are unstable, and, therefore, autoclaving in the container used to distribute it is not possible. During conventional sterilization, using the prescribed conditions, the decapeptide tends to decompose. To obtain an injectable solution it was therefore necessary to develop a lyophilizate.

The amount of active substance in the solution to be lyophilized is, however, so small that, in low active substance concentrations, only a loose fluff results on the glass wall of the ampoule after drying the solution free of auxiliary substances, and this fluff is carried out of the vial with the stream of water vapor generated by the sublimation process. It is therefore necessary to use a bulking agent that forms a stable cake. In high concentrations, this auxiliary substance can be dispensed with. The following auxiliary substances may be considered as bulking agents: hexitols, in particular mannitol, glucitol, sorbitol, such as D-sorbitol, dulcitol, allitol, altritol (for example D- and L-altritol), iditol (for example D- and L-iditol), their optically active forms (D- and L-forms) as well as the corresponding racemates. Nannitol is used in particular, such as D-mannitol, L-mannitol, DL-mannitol, sorbitol and/or dulcitol, and, of these, D-mannitol is preferred. The hexitol used may also be composed of a mixture of the hexitols named, for example a mixture of mannitol and sorbitol and/or dulcitol. Since dulcitol is less water soluble than, for example, mannitol, the dulcitol content in the aqueous solution should not exceed, for example, 3 percent by weight. Mannitol and sorbitol, on the other hand, can for example be mixed in any ratio.

Apart from hexitol it is also possible to add other, conventional pharmaceutical auxiliary substances, such as amino acids, such as alanine, glycine, lysine, phenylalanine, asparaginic acid, glutaminic acid, leucine, lactose, polyvinylpyrrolidone, glucose, fructose, albumin and equivalent bulking agents. Urea and sodium chloride may also be used as bulking agents. The total amount of such substances in the solution which is used for freeze-drying, is for example 0-16.9 parts by weight, for example 0.1-7 parts by weight, based on 1 part by weight of cetrorelix. In the finished lyophilizate the total amount of such auxiliary substances may be up to 16.9 parts by weight, based on one part by weight of hexitol. In detail, the amount of such auxiliary substances depends on the amount of hexitol present and to such an extent that the total amount of hexitol and such other auxiliary substances in the finished lyophilizate may not be more than a maximum of 17 parts by weight, based on 1 part by weight of cetrorelix. If only 0.1 part by weight of hexitol is present in the lyophilizate, it is thus possible to have up to 16.9 parts by weight of other auxiliary substances;

if, for example, 8.5 parts by weight of hexitol are present, the amount of other auxiliary substances may for example be up to 8.5 parts by weight, based on 1 part by weight of cetrorelix.

It was, however, found, during development work on the lyophilizate, that the active substance behaves in a widely variable and unpredictable manner during processing. The first batches gave good results, but it soon transpired that difficulties occurred during sterile filtration and faulty batches resulted.

It is known from the literature, for example from Powell, M. F.; Pharmaceutical Research, 1258-1263 (8)1991; Dathe, M: Int. J. Peptide Protein Res. 344-349 (36) 1990; Szejtli, J.: Pharmaceutical Technology International 16-22, 1991 that oligopeptides, particularly those with terminal acid amide function, tend to form gels. During sterile filtration this is apparent from the speed of filtration, indeed the increased viscosity of such solutions can often already be detected organoleptically. A gelatinous layer remains on the sterile filter. It is then no longer possible to prepare a medication with an exactly and reproducibly defined active substance content.

Table 1 lists various results of the first 11 batches.

The active substance contents fluctuate between 100% and 36%.

TABLE 1

Cetrorelix acetate

| Batch | Dosage | Active substance content % |
| --- | --- | --- |
| 1 | 100 µg | 100 |
| 2 | 500 µg | 100 |
| 3 | 500 µg | 90 |
| 4 | 500 µg | 36 |
| 5 | 500 µg | 100 |
| 6 | 500 µg | 85 |
| 7 | 1 mg | 80 |
| 8 | 1 mg | 100 |
| 9 | 2 mg | 100 |
| 10 | 2 mg | 80 |
| 11 | 2 mg | 100 |

To avoid this gel formation, the literature lists the following additives which may be tried out on an experimental basis:

Organic solvents may be considered, for example acetonitrile, n-butanol, tertiary butanol, ethanol, isopropanol, octanol and benzyl alcohol. It is also possible to use salts and buffer solutions, such as acetate buffer, citrate buffer, sodium chloride, sodium phosphate, sodium EDTA, sodium bicarbonate, phosphate buffer, guanidine acetate, urea.

Polymers may also be used, such as gelatin, polyethylene glycol 600, hydroxyethyl starch, polyvinylpyrrolidone, polyvinyl alcohol. The use of amino acids, for example alanine, glycine, lysine, phenylalanine, asparaginic acid, glutaminic acid and leucine has also been described. Acids that were used were citric acid, caprylic acid, octanoic acid, hydrochloric acid, sulphuric acid and acetic acid. Physiologically acceptable surfactants that may be used are benzalkonium chloride, cetyl alcohol, bile acids, lecithins, polysorbates, Spans® and Pluronics®.

Carbohydrates and cyclodextrins such as glucose, lactose, mannitol, saccharose, alpha-, beta- and gamma cyclodextrins, hydroxypropyl-alpha- and beta-cyclodextrins, hydroxyethyl cyclodextrins and methyl cyclodextrins have already been used. These auxiliary substances were tested as filtration supporting agents to prevent gel formation.

No satisfactory solution of the problem could, however, be found. Only acidification with acetic acid showed partial success. Here, too, it was, however, always necessary to accept high filtration losses.

SUMMARY OF THE INVENTION

It was then surprisingly found that peptides having 3-15 amino acids such as cetrorelix can be easily dissolved in 30% volume/volume acetic acid. The solution is then diluted to a final concentration of 3% peptide, e.g., cetrorelix, with water for injection purposes and mannitol is added. Although it is stated in the literature that the terminal amide group hydrolyzes easily in acid medium, this was not found in the case of cetrorelix. Solutions prepared according to this method caused no difficulties during filtration. The correct amounts of active substance were always found.

Thus, in accordance with the present invention, a peptide which contains 3-15 amino acids is dissolved in acetic acid to form a solution containing 100-10,000 parts by weight of acetic acid for each part of peptide, the solution is transferred to water, and the resulting solution is lyophilized.

The filtration speed of the acetic acid solution attains values that ensure satisfactory production sequences. A general process for sterile lyophilization is described in pages 557-559 of Sucker, Fuchs and Speiser (Publishers) "Pharmazeutische Technologie" 2nd edition 1991, Thieme-Verlag, Stuttgart-New York. A further description of the lyphilization process used is given in German published specification (DOS) 37 35 614 (U.S. Pat. No. 5,204,335).

The lyophilizate is used in the treatment of female sterility. One therapeutic process has hitherto consisted in stimulating follicle maturation using human menopause gonadotrophin and then triggering ovulation by administering human chorion gonadotrophin. The ovulation triggered thereby occurred 32 hours later. The resulting ova are available for in vitro fertilization.

A disadvantage of this treatment with agonists is the fact that up to 10 follicles mature during the stimulation phase. This elevated follicle maturation leads to hormone level peaks in the LH. These peaks result in an early stage of follicle maturation and ovulation at an unpredicted point in time. This impaired ovulation occurs in about 25% of treated cases and is a disadvantage since the cycle that displays disturbed ovulation of this kind cannot be used for the collection of ova and the entire treatment has to be repeated about 1 month later.

Another disadvantage of the conventional simulation treatment and the use of LHRH agonists in order to avoid premature LH-peaks is the long treatment duration of 4 weeks which is needed to achieve satisfactory suppression. The agonists continue to display a hyperstimulation syndrome in 1-2% of cases in which the follicle cells hypertrophy. The risk of hyperstimulation is particularly great in the case of polycystic ovaries. The hyperstimulation syndrome is a severe side effect which can lead to fatalities.

It has now been found that the antagonist cetrorelix displays the following advantages in this treatment:

Treatment with cetrorelix over 5 days is sufficient to achieve total suppression. The premature LH peaks cannot arise and the frequency of hyperstimulation syndrome should be reduced. In addition, less HMG is used in the 2nd phase of therapy, the ovulation triggering phase. This gives this in-vitro fertilization treatment a not inconsiderable cost advantage. In-vitro fertilization is, for example, used when a tube anomaly is present. To perform this treatment it is necessary to precisely monitor the cycle and to establish the time of ovulation as precisely as possible. This has hitherto only been achieved to a limited extent since preovulatory LH increase often occurred too early due to simulation with HMG/HCG, or was not maintained for a sufficiently long period. Avoidance of this premature increase is, however, of critical importance for the success of the treatment in order to precisely determine the time of fertilization. This reduces the physical and mental burden on the patient and makes optimum use of hospital logistics. To achieve this objective with great reliability it is necessary to suppress endogenous hormone production (LH-FSH, oestradiol) as completely as possible in order to simultaneously stimulate follicle maturation through administration of exogenous gonadotrophins (HMG/HCG) and to monitor the hormone status at any time. It is only when a sufficiently large number of follicles have been achieved (4-6), having approximately the same degree of-maturation, that ovulation is triggered by administering an HCG bolus injection.

Use of an antagonist makes treatment substantially more successful and safer for the patient.

Another area of use of the cetrorelix lyophilizate according to the present invention is to protect the gonads in male patients. Male patients are pre-treated with cetrorelix lyophilizate and the activity of the gonads is reinforced. As a result, other harmful noxious agents, such as radiation therapy or treatment with cytostatics, have no or only a small possibility of affecting the sensitive tissue of the gonads.

DETAILED DESCRIPTION OF PREFERRED EMBODIMENTS

The following Examples illustrate the invention.

EXAMPLE 1

Approx. 1.5 liters of water for injection purposes are prepared in a suitable glass vessel. 210 g water for injection purposes are prepared in another glass vessel and 91.17 g acetic acid are added. The amount of cetrorelix acetate calculated (1.62-1.695 g, depending on the content of the batch used) is dissolved in the prepared 30% acetic acid with stirring. This solution is transferred to the glass vessel with 1.5 liters of water for injection purposes, 82.2 g mannitol are added, dissolved and made up to 3039 g with water for injection purposes.

In-process checks:

pH value: 2.5-3.0

Density: 1.009-1.017 g/cm$^3$ at 20°C.

Refractive index:

1.227-1.340 at 440 nm and 20° C.

The solution is sterilized by filtration through an appropriate membrane filter (pore size 0.2 μm) under aseptic conditions. 100 ml first runnings should be discarded. The filters should be sterilized with superheated steam before sterile filtration. Cetrorelix freeze-dried solution should be protected from recontamination during storage.

The solution is immediately filled into colorless injection bottles DIN 2R, hydrolytic class I under aseptic conditions and provided with sterile freeze-drying stoppers. The nominal filling amount is 2.0 ml=2.026 g.

The 2 ml injection bottles were rinsed in an injection bottle washing machine, dried with hot air and sterilized. The cleaned, freeze-drying stoppers were autoclaved. The closed injection bottles were transferred to a freeze-drying installation and frozen at a plate temperature of −40° C. Drying was carried out using a drying program with a plate temperature of −40° C. rising to +20° C. The installation is then flooded with sterile nitrogen, the bottles are closed in the installation and the stoppers secured with crimped caps.

The injection bottles are checked visually for faulty closures and outer faults. Faulty injection bottles are removed and destroyed.

Cetrorelix lyophilizate 1 mg is a white, solid, freeze-dried cake in a colorless 2 ml injection bottle which is closed with gray freeze-drying stoppers and yellow flip-off crimped caps.

EXAMPLE 2

Nonapeptide (Bombesin-Antagonist)

420 g water for injection purpose are prepared in a suitable vessel and 121.56 g acetic acid are added. The amount of the nonapeptide (about 3.783 g, depending on the content of the batch used) is dissolved in the prepared 20% acetic acid and with stirring. 82., 2 niannitol are added and dissolved. This solution is sterilized by filtration through an appropriate membrane filter (pore size 0.2 μm) under aseptic conditions. The same membrane filter is used for the water for injection purpose to make up the solution to 3064 g. The filters should be sterilized with superheated steam.

| In-process checks: | |
| --- | --- |
| pH value: | 2.5-3.0 |
| Density: | 1.0213-1.0225 g/cm$^3$ at 20° C. |
| Refractive Index: | 1.335-1.345 at 589 nm at 20° C. |

The solution should be protected from recontamination during storage. The solution is filled in to sterile colorless injection bottles DIN 2 R, hydrolytic class I under aseptic conditions and provided with sterile freeze-drying stoppers. The nominal filling amount is 1.0 ml=1.022 g.

The 2 ml injection bottles were rinsed in an injection bottle washing machine, dried with hot air and sterilized. The cleaned freeze-drying stoppers were autoclaved. The injection bottles were transferred to a freeze-drying installation and frozen at a plate temperature of −40° C.

Drying was carried out using a drying programme with a plate temperature of −40° C. rising to +20° C. The installation is then flooded with sterile nitrogen, the bottles are closed in the installation and the stoppers are sealed with crimped caps.

The injection bottles are checked visually for faulty closures and outer faults. Faulty injection bottles are removed and destroyed.

The lyophilisate of the nonapeptide (1 mg) is a white, solid, freeze-dried cake in a colorless 2 ml injection bottle which is closed with grey freeze-drying stoppers and flip-off crimped caps.

EXAMPLE 3

Tripeptide (Protirelin)

143.5 g water for injection purpose are prepared in a suitable vessel and 61.5 g acetic acid are added. The amount of the Protirelin acetate calculated (equivalent to 800 mg of the peptide base) is dissolved with stirring. This solution is transferred to another vessel with approximately 1 l water for injection purpose. 109.6 g mannitol are added, dissolved and made up to 2048 g with water for injection purposes.

| In-process checks: | |
| --- | --- |
| pH value: | 2.5-3.0 |
| Density: | 1.0232-1.0252 g/cm$^3$ at 20° C. |
| Refractive Index: | 1.334-1.344 at 589 nm at 20° C. |

The solution is filled in to sterile colorless injection bottles DIN 2 R, hydrolytic class I under aseptic conditions and provided with sterile freeze-drying stoppers. The nominal filling amount is 1.0 ml=1.024 g.

The 2 ml injection bottles were rinsed in an injection bottle washing machine, dried with hot air and sterilized. The cleaned freeze-drying stoppers were autoclaved. The injection bottles were transferred to a freeze-drying installation and frozen at a plate temperature of −40° C.

Drying was carried out using a drying programme with a plate temperature of −40° C. rising to +20° C. The installation is then flooded with sterile nitrogen, the bottles are closed in the installation and the stoppers are sealed with crimped caps.

The injection bottles are checked visually for faulty closures and outer faults. Faulty injection bottles are removed and destroyed.

The Protireline lyophilizate (0.4 mg) is a white, solid, freeze-dried cake in a colorless 2 ml injection bottle which is closed with grey freeze-drying stoppers and flip-off crimped caps.

EXAMPLE 4

Tetradecapeptide (Somatostatin)

245 g water for injection purpose are prepared in a suitable vessel and 61.5 g acetic acid are added. The amount of somatostatine acetate calculated (0.52-0.66 g, dependent on the content of the batch used) is dissolved with stirring. This solution is transferred to another vessel with approximately 1 l water for injection purpose. 109.6 g mannitol are added, dissolved and made up to 2049 g with water for injection purposes.

| In-process checks: | |
| --- | --- |
| pH value: | 2.5-3.0 |
| Density: | 1.0235-1.0255 g/cm$^3$ at 20° C. |
| Refractive Index: | 1.336-1.348 at 589 nm at 20° C. |

The solution is filled in to sterile colorless injection bottles DIN 2 R, hydrolytic class I under aseptic conditions and provided with sterile freeze-drying stoppers. The nominal filling amount is 1.0 ml=1.024 g.

The 2 ml injection bottles were rinsed in an injection bottle washing machine, dried with hot air and sterilized. The cleaned freeze-drying stoppers were autoclaved. The injection bottles were transferred to a freeze-drying installation and frozen at a plate temperature of −40° C.

Drying was carried out using a drying programme with a plate temperature of −40° C. rising to +20° C. The installation is then flooded with sterile nitrogen, the bottles are closed in the installation and the stoppers are sealed with crimped caps.

The injection bottles are checked visually for faulty closures and outer faults. Faulty injection bottles are removed and destroyed.

The lyophilizate (0.25 mg somatostatine acetate) is a white, solid, freeze-dried cake in a colorless 2 ml injection bottle which is closed with grey freeze-drying stoppers and flip-off crimped caps.

What is claimed is:

1. A sterile Cetrorelix acetate-bulking agent lyophilisate prepared by a method comprising the steps of:
   (a) dissolving having the amino acid sequence of Ac-D-Nal(2)-D-pCl-Phe-D-Pal(3)-Ser-Tyr-D-Cit-Leu-Arg-Pro-D-Ala-NH$_2$ (SEQ ID NO: 1) in 30% (v/v) aqueous acetic acid to form a solution;
   (b) diluting the solution with water;
   (c) adding bulking agent to the solution, after which the solution has a pH range between 2.5-3.0;
   (d) sterilizing the solution by filtration; and
   (e) lyophilizing the solution, producing a sterile Cetrorelix acetate lyophilisate-bulking agent thereby.

2. The sterile Cetrorelix acetate-bulking agent lyophilisate according to claim 1 wherein the bulking agent is a conventional pharmaceutical auxiliary selected from the group consisting of amino acids, polyvinylpyrrolidone, albumin, a hexitol, urea, and sodium chloride.

3. The sterile Cetrorelix acetate-bulking agent lyophilisate according to claim 2 wherein the hexitol is selected from the group consisting of mannitol, glucitol, sorbitol, D-sorbitol, dulcitol, allitol, and iditol, and wherein the bulking agent in the lyophilisate is in an amount from 0.1 to 17 parts by weight per 1 part by weight of the peptide.

4. The sterile Cetrorelix acetate-bulking agent lyophilisate according to claim 1 wherein 1 part by weight of the peptide is dissolved in 100-10,000 parts by weight 30% (v/v) aqueous acetic acid and wherein the solution is diluted with water to 3% (v/v) aqueous acetic acid and wherein the bulking agent is mannitol.

* * * * *

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Nal(2)
<220> FEATURE:
<221> NAME/KEY: MOD_RES
<222> LOCATION: (2)
<223> OTHER INFORMATION: D-pCl-Phe
<220> FEATURE:
<221> NAME/KEY: MOD_RES
<222> LOCATION: (3)
<223> OTHER INFORMATION: D-Pal(3)
<220> FEATURE:
<221> NAME/KEY: MOD_RES
<222> LOCATION: (6)
<223> OTHER INFORMATION: D-Cit
<220> FEATURE:
<221> NAME/KEY: MOD_RES
<222> LOCATION: (10)
<223> OTHER INFORMATION: D-Ala
<220> FEATURE:
<223> OTHER INFORMATION: n-term acetylation
<220> FEATURE:
<223> OTHER INFORMATION: c-term amidation

<400> SEQUENCE: 1

Xaa Phe Xaa Ser Tyr Xaa Leu Arg Pro Ala
 1               5                  10
```